(12) United States Patent
Slaghuis et al.

(10) Patent No.: US 9,493,736 B2
(45) Date of Patent: Nov. 15, 2016

(54) METHOD FOR LYSING CELLS

(75) Inventors: Joerg Slaghuis, Darmstadt (DE); Peter Rossmanith, Gaaden (AT); Sabine Fuchs, Kirchstetten (AT); Patrick Julian Mester, Vienna (AT); Martin Wagner, Vienna (AT)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/113,221

(22) PCT Filed: Mar. 28, 2012

(86) PCT No.: PCT/EP2012/001363
§ 371 (c)(1),
(2), (4) Date: Oct. 22, 2013

(87) PCT Pub. No.: WO2012/146338
PCT Pub. Date: Nov. 1, 2012

(65) Prior Publication Data
US 2014/0051088 A1    Feb. 20, 2014

(30) Foreign Application Priority Data
Apr. 27, 2011 (EP) .................................. 11003449

(51) Int. Cl.
C07H 21/00 (2006.01)
C12Q 1/68 (2006.01)
C12N 1/06 (2006.01)

(52) U.S. Cl.
CPC .............. C12N 1/06 (2013.01); C12Q 1/6806 (2013.01)

(58) Field of Classification Search
CPC .............................. C12N 1/06; C12Q 1/6806
USPC ........................ 536/25.4; 435/6.1; 422/430
See application file for complete search history.

(56) References Cited

U.S. PATENT DOCUMENTS

| 5,827,602 A | 10/1998 | Koch et al. |
| 7,129,344 B1 * | 10/2006 | Butt et al. ................. 536/25.4 |
| 8,303,818 B2 | 11/2012 | Salvo et al. |
| 2006/0141556 A1 | 6/2006 | Jeong et al. |
| 2006/0240409 A1 | 10/2006 | Prince et al. |
| 2010/0184210 A1 | 7/2010 | Rossmanith et al. |
| 2011/0053251 A1 | 3/2011 | Birkner et al. |

(Continued)

FOREIGN PATENT DOCUMENTS

| CN | 1190435 A | 8/1998 |
| CN | 101268198 A | 9/2008 |

(Continued)

OTHER PUBLICATIONS

Stratagene Catalog 1988 p. 39.*

(Continued)

*Primary Examiner* — Jezia Riley
(74) *Attorney, Agent, or Firm* — Millen White Zelano and Branigan, PC; Csaba Henter; Anthony Zelano

(57) ABSTRACT

The present invention relates to a method for the lysis of cells, especially bacterial cells and the isolation of nucleic acids. The sample is treated with lysis solution that comprises at least one liquid that is not miscible with water and heated. Afterwards the mixture is cooled down and water is added so that after cooling a two phase system is generated. The nucleic acids can be found in the aqueous phase.

13 Claims, 4 Drawing Sheets

(56) References Cited

U.S. PATENT DOCUMENTS

2011/0076748 A1 3/2011 Salvo et al.
2012/0122110 A1 5/2012 Rossmanith et al.

FOREIGN PATENT DOCUMENTS

| EP | 2049677 A1 | 4/2009 |
| EP | 2302030 A1 | 3/2011 |
| WO | 96/36706 A1 | 11/1996 |
| WO | 9636706 A1 | 11/1996 |
| WO | 2006088601 A2 | 8/2006 |
| WO | 2008017097 A1 | 2/2008 |
| WO | 2010145754 A1 | 12/2010 |

OTHER PUBLICATIONS

Office Action related to corresponding Chinese Patent Application No. 201280020268.0 dated Sep. 3, 2014.
International Search Report from PCT/EP2012/001363 dated Sep. 4, 2012.
Patrick Mester et al. "Use of Ionic Liquid-Based Extraction for Recovery of *Salmonella* Typhimurium and Listeria monocytogenes from Food Matrices" Journal of Food Protection, vol. 71, No. 4, [2010], pp. 680-687.
Eva Mayrl et al. "Broad Range Evaluation of the Matrix Solubilization (Matrix Lysis) Strategy for Direct Enumeration of Foodborne Pathogens by Nucleic Acids Technologies" Journal of Food Protection, vol. 72, No. 6, [2009], pp. 1225-1233.
Holger Pfruender et al. "Water immiscible ionic liquids as solvents for whole cell biocatalysis" Journal of Biotechnology, vol. 124, [2006], pp. 182-190.
Rodrigo E. Teixeira "Energy-efficient extraction of fuel and chemical feedstocks from algae" Green Chemistry, vol. 14, [2012], pp. 419-427.
Sabine Fuchs et al. "Ionic liquids for DNA quantification out of Gram negative and Gram positive bacteria" University of Veterinary Medicine, Vienna, Austria—XP-002681882, [Sep. 2011], 1 page.
Jian-Hua Wang et al. "Direct Extraction of Double-Stranded DNA Into Ionic Liquid 1-Butyl-3-methylimidazolium Hexafluorophosphate and its Quantification" Analytical Chemistry, vol. 79, No. 2, [Jan. 2007], pp. 620-625.
Fernanda M. Da Silva Tatley et al. "Plasmid profiles of "Campylobacter upsaliensis" isolated from blood cultures and stools of paediatric patients" Journal of Medical Microbiology, vol. 37, No. 1, [Jul. 1992], pp. 8-14.
Peter Rossmanith et al. "Detection of Listeria monocytogenes in food using a combined enrichment/real-time PCR method targeting the prfA gene" Research in Microbiology, vol. 157, [2006], pp. 763-771.
Barbara Roeder et al. "Autonomous Growth of Isolated Single Listeria moncytogenes and *Salmonella enterica* Serovar Typhimurium Cells in the Absence of Growth Factors and Intercellular Contact" Applied and Environmental Microbiology, vol. 76, No. 8, [Apr. 2010], pp. 2600-2606.
E. Kaclikova et al. "Quantification of Escherichia coli by kinetic 5'-nuclease polymerase chain reaction (real-time PCR) oriented to sfmD gene" Letters in Applied Microbiology, vol. 41, [2005], pp. 132-135.
Karin Fruhwirth et al. "Cloning and Characterisation of a Δ-prfA Listeria monocytogenes Strain Containing an Artificial Single Copy Genomic Internal Amplification Control (IAC) for Use as Internal Sample Process Control (ISPC)" Food Analytical Methods, DOI 10.1007/s12161-011-9212-6, [Mar. 2011], 11 pages.
M. D'Agostino et al. "A Validated PCR-Based Method to Detect Listeria monocytogenes Using Raw Milk as a Food Model-Towards an International Standard" Journal of Food Protection, vol. 67, No. 8, [2004], pp. 1646-1655.
Rika Hagiwara, et al. "Room temperature ionic liquids of alkylimidazolium cations and fluoroanions" Journal of Fluorine Chemistry, vol. 105, [2000], pp. 221-227.
Thomas Welton "Room-Temperature Ionic Liquids. Solvents for Synthesis and Catalysis" Chem. Rev., vol. 99, [1999], pp. 2071-2083.
Marlyn J. Earle et al. "Ionic Liquids. Green Solvents for the Future" Pure Appl. Chem., vol. 72, No. 7, [2000], pp. 1391-1398.
Roger Sheldon "Catalytic reactions in ionic liquids" Chem. Commun., [2001], pp. 2399-2407.
Chandra Mohan "Calbiochem—Buffers, A guide for the preparation and use of buffers in biological systems" EMD [1999], 38 pages.

* cited by examiner

N,N-dimethyl-ethanolammonium    propionate [DMAE][prop]

Trihexyl(tetradecyl)phosphonium
tris(pentafluorethyl)trifluorophosphate
[Ttp][Fap]

1-Butyl-1-methylpyrrolidinium
bis(trifluormethylsulfonyl)imide
[bmpyrr][Ntf$_2$]

METHOD FOR LYSING CELLS

The present invention relates to a method for the lysis of cells, especially bacterial cells and the isolation of nucleic acids. The sample is treated with a lysis solution that comprises at least one liquid that is not miscible with water and heated. Afterwards the mixture is cooled down and water is added so that after cooling a two phase system is generated. The nucleic acids can be found in the aqueous phase.

BACKGROUND OF THE INVENTION

Nucleic acids such as DNA, are used extensively in the field of molecular biology for research and clinical analyses. Common methods for analyzing DNA are Southern blotting, amplification through methods such as polymerase chain reaction (PCR), and sequencing. Using these methods, differences in DNA sequence are determined to aid in gene identification, population screening, pathogen identification and diagnostic testing. All of these analyses require purified DNA samples as the basis for consistent and valid results.

The analysis and in vitro manipulation of nucleic acids is typically preceded by a nucleic acid isolation step in order to free the nucleic acid from unwanted contaminants which may interfere with subsequent processing procedures. For the vast majority of procedures in both research and diagnostic molecular biology, extracted nucleic acids are required as the first step. In a typical DNA extraction protocol, cells containing the nucleic acid of interest are harvested and lysed.

Cell lysis is a process of releasing materials out of a cell by disrupting the cell membrane, and in particular, a process of extracting intracellular materials from a cell to isolate DNA or RNA before further processing with nucleic acid based methods such as PCR and cloning techniques.

Cell lysis methods through cell rupture can be classified into mechanical methods and non-mechanical methods.

Mechanical methods include ultrasonication, disruption using a homogenizer, pressing using, for example, a French press, etc., decompression, pulverization, etc. Non-mechanical methods include chemical methods, thermal methods, enzymatic methods, etc.

Chemical methods, which are non-mechanical methods, use, for example, an acid, a base, a detergent, a solvent, a chaotropic reagent, etc. Especially, a chemical method using a detergent is widely used. Detergents disrupt a lipid double membrane to release cell contents and lyses membrane protein. Detergents are most commonly used to lyse animal cells. Most detergents denature protein. However, a reagent for cell lysis is separately added, and hence a subsequent process of removing the reagent is required. PCR inhibition may occur, and the process takes a long time.

Enzymatic methods use lysozyme, protease, etc.

Thermal methods include freezing-thawing, heating, osmotic impact, electric impact, etc. For example, cell lysis is achieved by contacting cells with a hot object, such as a hot plate, or by repeating a cycle of freezing to −70° C. and thawing to room temperature.

In US 2006/0141556 cell lysis is performed by raising the temperature of the sample by radiating microwaves onto the sample. An increase in vapour pressure is prevented by adding zwitterionic compounds or ionic liquids to the sample.

There is still need for a fast and effective lysis method.

BRIEF DESCRIPTION OF THE INVENTION

It has been found that cells, especially bacterial cells, can be effectively lysed by adding to the sample a lysis solution comprising a water-immiscible liquid, heating the mixture and after cooling, adding water or an aqueous buffer to generate a two phase system. The nucleic acids can be found in the aqueous phase and can be directly transferred to further downstream manipulations like PCR.

Therefore the present invention is directed to a method for lysing cells by
a) providing a sample comprising the cells
b) adding a lysis solution at least comprising a water-immiscible liquid to the sample
c) heating the mixture obtained in step b) to a temperature above 80° C.
d) in case the temperature in step c) was above 100° C., cooling the sample to a temperature below 100° C.
e) adding water or an aqueous buffer solution to the mixture, thereby generating a water-immiscible liquid phase and an aqueous phase In a preferred embodiment the cells are bacterial cells.

In a preferred embodiment the mixture is heated to a temperature between 100 and 150° C.

In a preferred embodiment in step d), the sample is cooled to a temperature between 20 and 40° C.

In a preferred embodiment, the lysis solution added in step b) comprises at least one oil or at least one ionic liquid. In a very preferred embodiment, it comprises at least one ionic liquid.

In a preferred embodiment the lysis solution added in step b) comprises at least one bis(trifluormethylsulfonyl)imide [Ntf$_2$] based ionic liquid. That means the anion of the ionic liquid is bis(trifluormethylsulfonyl)imide [Ntf$_2$].

In a preferred embodiment the lysis solution added in step b) comprises Trihexl(tetradecyl)phosphoniumtris(pentafluorethyl)trifluorophosphate [Ttp][Fap] and/or 1-Butyl-1-methylpyrrolidiniumbis(trifluormethylsulfonyl)imide [bmpyrr][Ntf$_2$].

In one embodiment which is especially preferred for gram positive cells, prior to adding the lysis solution, in a step b1) the sample is preincubated with at least one N,N-dimethyl-ethanolammonium [DMAE] based ionic liquid. That means the cation of the ionic liquid is N,N-dimethyl-ethanolammonium [DMAE].

In one embodiment, after step e), the resulting mixture is incubated with a proteinase.

In one embodiment, after step e) and after the optional incubation with a proteinase, the nucleic acids in the aqueous phase are directly analyzed by PCR methods, in particular by real time PCR, electroporesis (agarose or polyacrylamide) or cloning techniques like ligation or restriction enzyme digest.

The present invention also relates to a kit comprising one container with a water-immiscible liquid and one container with a proteinase.

DESCRIPTION OF THE INVENTION

The term "nucleic acid" as used herein, refers to any type of DNA or RNA known to a person skilled in the art. Examples are genomic DNA, messenger RNA, plasmid DNA.

The term "buffer" as used herein, refers to aqueous solutions or compositions that resist changes in pH when acids or bases are added to the solution or composition. This resistance to pH change is due to the buffering properties of such solutions. Thus, solutions or compositions exhibiting buffering activity are referred to as buffers or buffer solutions. Buffers generally do not have an unlimited ability to maintain the pH of a solution or composition. Rather, they are typically able to maintain the pH within certain ranges, for example between pH 7 and pH 9. Typically, buffers are able to maintain the pH within one log above and below their pKa (see, e.g. C. Mohan, Buffers, A guide for the preparation and use of buffers in biological systems, CALBIOCHEM, 1999). Buffers and buffer solutions are typically made from buffer salts or preferably from non-ionic buffer components like TRIS and HEPES. The buffer which may be used in the method of the present invention is preferably selected from the group of phosphate buffer, phosphate buffered saline buffer (PBS), 2-amino-2-hydroxymethyl-1,3-propanediol (TRIS) buffer, TRIS buffered saline buffer (TBS) and TRIS/EDTA (TE).

The cells to be lysed with the method according to the present invention are all types of cells, preferably cells comprising a cell wall, most preferably bacterial cells, fungal cells, archaeal cells, algae cells or plant cells. Particularly preferred cells are Gram-positive or Gram-negative bacterial cells, especially those selected from the group consisting of *Listeria* spp., *S. aureus*, *P. paratuberculosis*, *Salmonella* spp., *C. jejuni*, *Penicillum roquefortii* and *E. Coli*.

According to the present invention the sample may be any sample comprising cells. The sample may be for example a food sample, a body fluid, in particular blood, plasma or serum, water or a tissue sample. In a preferred embodiment the sample has been generated from a complex sample with a method comprising the steps of:
a) providing a complex sample,
b) incubating said sample with:
  at least one chaotrope,
  a buffer and
  at least one detergent,
c) isolating said cells from the resulting mixture by centrifugation or filtration.

Details about this procedure of isolating cells from a complex sample are disclosed in EP 2049677.

The sample according to the present invention can also be generated from a complex sample by
a) providing a complex sample,
b) incubating said sample with an extraction solution that comprises at least $MgCl_2$ and/or an ionic liquid
c) isolating said cells from the mixture of step b), preferably by centrifugation, affinity binding and/or filtration.

Details about this procedure of isolating cells from a complex sample are disclosed in WO 2010145754.

According to the present invention a complex sample may be for example a food sample, a body fluid, in particular blood, plasma or serum, water or a tissue sample. Typically complex samples have a complex matrix (i.e. comprising among others proteins, lipids, carbohydrates etc.) and/or a high viscosity.

According to the present invention, a water-immiscible liquid is a water-immiscible oil or a water-immiscible ionic liquid.

An oil suitable for the method according to the present invention is any oil that is liquid at room temperature and has a boiling point as well as a flash point above 150° C., more preferred above 200° C. In addition the oil needs to be water-immiscible. That means the oils suitable for the method according to the present invention form a two-phase system when mixed with water at temperatures between 20 and 80° C. Examples for suitable oils are organic oils, mineral oils, silicon oils or essential oils.

Organic oils are oils comprising at least fatty acids and/or triglycerides. Organic oils that are liquid at room temperature typically comprise mono- or poly-unsaturated fatty acids of a chain length between 6 and 30 carbon atoms. Example of suitable organic oils are rapeseed oil and castor oil.

Mineral oils are oils comprising paraffin oils and or naphthemic oils and/or aromatic oils. Preferred mineral oils are paraffin oils comprising a mixture of heavier alkanes, like heavy white oil (CAS 8012-95-1).

Suitable silicon oils preferably are linear silicon oils of the general formula $R(R_2SiO)_nSiR_3$, R being, independently from one another but preferably identical in the whole molecule, a straight or branched C1 to C8 alkyl residue. One example of a suitable silicon oil is poly(dimethylsiloxane) (CAS 63148-62-9).

Examples for essential oils are terpenes or terpenoids.

Ionic liquids or liquid salts as used in the present invention are ionic species which consist of a typically organic cation and an anion. They do not contain any neutral molecules and usually have melting points below 373 K.

The area of ionic liquids is currently being researched intensively since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227).

In general, all ionic liquids of the general formula $K^+A^-$ known to the person skilled in the art, in particular those which are immiscible with water, are suitable in the method according to the invention.

The anion $A^-$ of the ionic liquid is typically selected from the group comprising halides, tetrafluoroborate or derivatives, hexafluorophosphate or derivatives like $PF_3(R_f)_3$, cyanamide, thiocyanate or imides of the general formula $[N(R_f)_2]^-$ or of the general formula $[N(XR_f)_2]^-$, Where $R_f$ Denotes Partially or Fully Fluorine-Substituted alkyl having 1 to 8 C atoms and X denotes $SO_2$ or CO. The halide anions here can be selected from chloride, bromide and iodide anions, preferably from chloride and bromide anions.

There are no restrictions per se with respect to the choice of the cation $K^+$ of the ionic liquid. However, preference is given to organic cations, particularly preferably ammonium, phosphonium, uronium, thiouronium, guanidinium cations or heterocyclic cations like pyrrolidinium cations.

Ammonium cations can be described, for example, by the formula (1)

$$[NR_4]^+ \qquad (1),$$

where
R in each case, independently of one another, denotes
H, where all substituents R cannot simultaneously be H,
OR', NR'$_2$, with the proviso that a maximum of one substituent R in formula (1) is OR', NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more R may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R' O—, —C(O)NR'—, —SO$_2$NR'—, —OP(O)R'O—, —P(O)(NR'$_2$)NR'—, —PR'$_2$=N— or —P(O)R'— where R' may be =H, non-, partially or perfluorinated C$_1$- to C$_6$-alkyl, C$_3$- to C$_7$-cycloalkyl, unsubstituted or substituted phenyl and X may be =halogen.

Phosphonium cations can be described, for example, by the formula (2)

$$[PR^2_4]^+ \quad (2),$$

where
R$^2$ in each case, independently of one another, denotes
H, OR' or NR'$_2$
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more R$^2$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R$^2$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_6$-alkyl, C$_3$- to C$_7$-cycloalkyl, unsubstituted or substituted phenyl and X=halogen.

However, cations of the formulae (1) and (2) in which all four or three substituents R and R$^2$ are fully substituted by halogens are excluded, for example the tris(trifluoromethyl) methylammonium cation, the tetra(trifluoro-methyl)ammonium cation or the tetra(nonafluorobutyl)ammonium cation.

Uronium cations can be described, for example, by the formula (3)

$$[(R^3R^4N)—C(=OR^5)(NR^6R^7)]^+ \quad (3),$$

and thiouronium cations by the formula (4), $$[(R^3R^4N)—C(=SR^5)(NR^6R^7)]^+ \quad (4),$$

where
R$^3$ to R$^7$ each, independently of one another, denotes
hydrogen, where hydrogen is excluded for R$^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more of the substituents R$^3$ to R$^7$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R$^3$ to R$^7$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_6$-alkyl, C$_3$- to C$_7$-cycloalkyl, unsubstituted or substituted phenyl and X=halogen.

Guanidinium cations can be described by the formula (5)

$$[C(NR^8R^9)(NR^{10}R^{11})(NR^{12}R^{13})]^+ \quad (5),$$

where
R$^8$ to R$^{13}$ each, independently of one another, denotes
hydrogen, —CN, NR'$_2$, —OR'
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more of the substituents R$^8$ to R$^{13}$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R$^8$ to R$^{13}$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O) R'O—, —P(O)(NR'$_2$)NR'—, —PR'$_2$=N— or —P(O)R'— where R'=H, non-, partially or perfluorinated C$_1$- to C$_6$-alkyl, C$_3$- to C$_7$-cycloalkyl, unsubstituted or substituted phenyl and X=halogen.

In addition, it is possible to employ cations of the general formula (6)

$$[HetN]^+ \quad (6),$$

where
HetN$^+$ denotes a heterocyclic cation selected from the group

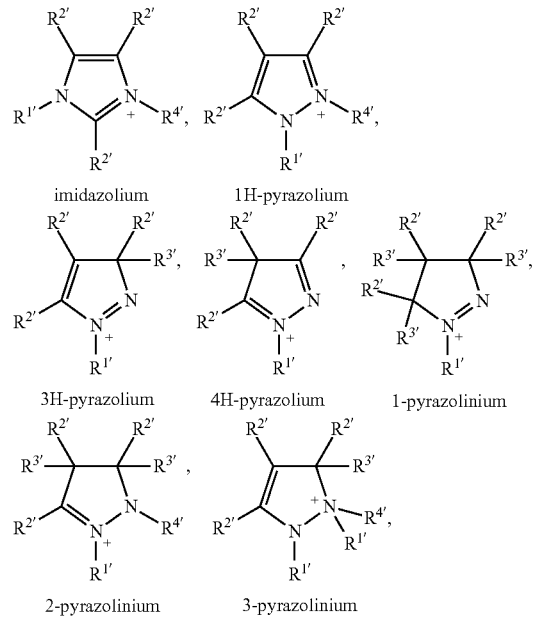

-continued

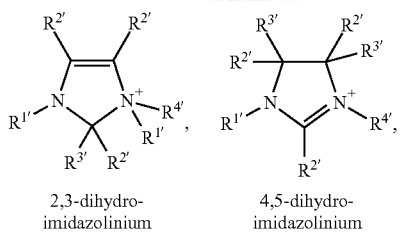

2,3-dihydro-imidazolinium     4,5-dihydro-imidazolinium

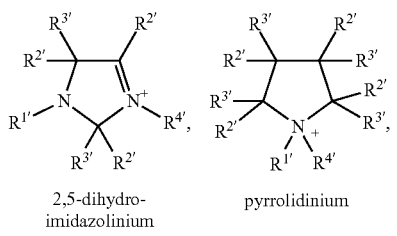

2,5-dihydro-imidazolinium     pyrrolidinium

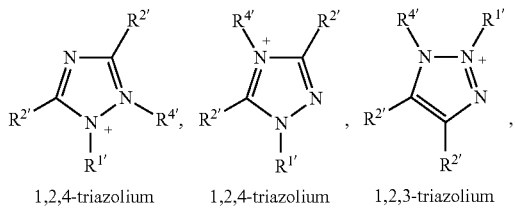

1,2,4-triazolium    1,2,4-triazolium    1,2,3-triazolium

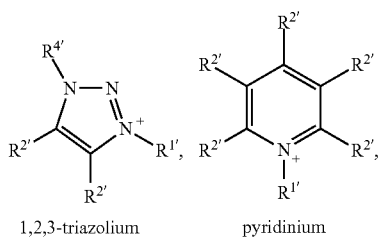

1,2,3-triazolium     pyridinium

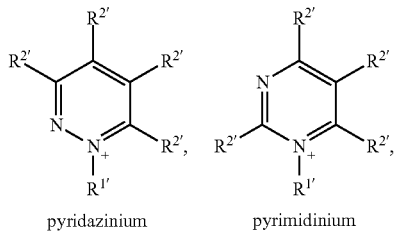

pyridazinium     pyrimidinium

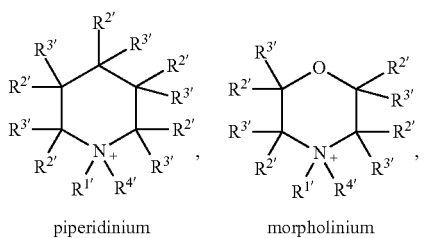

piperidinium     morpholinium

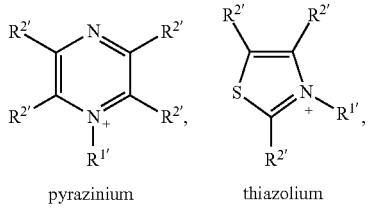

pyrazinium     thiazolium

-continued

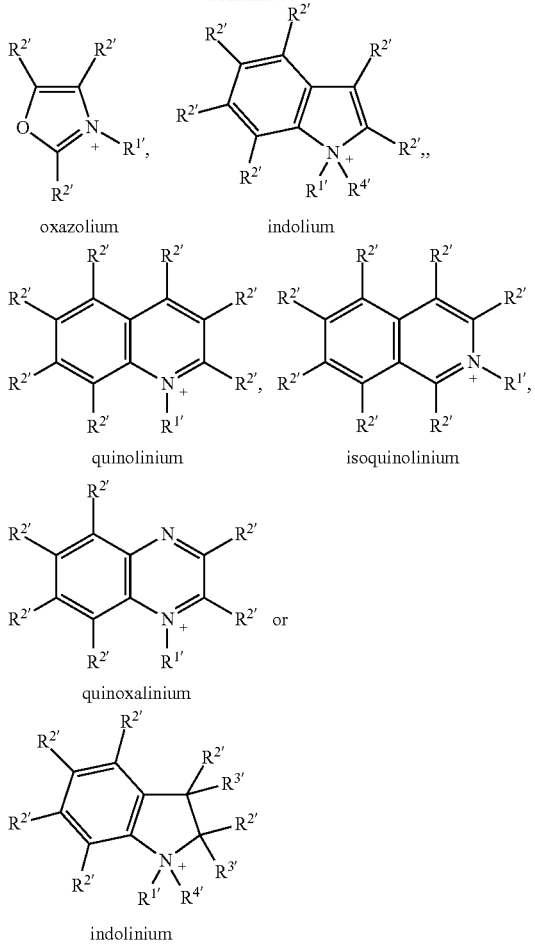

where the substituents
$R^{1'}$ to $R^{4'}$ each, independently of one another, denote hydrogen, —CN, —OR', —NR'$_2$, —P(O)R'$_2$, —P(O)(OR')$_2$, —P(O)(NR'$_2$)$_2$, —C(O)R', —C(O)OR',
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
saturated, partially or fully unsaturated heteroaryl, heteroaryl-C$_1$-C$_6$-alkyl or aryl-C$_1$-C$_6$-alkyl,
where the substituents $R^{1'}$, $R^{2'}$, $R^{3'}$ and/or $R^{4'}$ together may also form a ring system,
where one or more substituents $R^{1'}$ to $R^{4'}$ may be partially or fully substituted by halogens, in particular —F and/or —Cl, or —OH, —OR', —CN, —C(O)OH, —C(O)NR'$_2$, —SO$_2$NR'$_2$, —C(O)X, —SO$_2$OH, —SO$_2$X, —NO$_2$, but where $R^{1'}$ and $R^{4'}$ cannot simultaneously be fully substituted by halogens, and where, in the substituents $R^{1'}$ to $R^{4'}$, one or two non-adjacent carbon atoms which are not bonded to the heteroatom may be replaced by atoms and/or atom groups selected from the —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated $C_1$- to $C_6$-alkyl, $C_3$- to $C_7$-cycloalkyl, unsubstituted or substituted phenyl and X=halogen.

For the purposes of the present invention, fully unsaturated substituents are also taken to mean aromatic substituents.

The water-immiscible ionic liquids that are suitable for the method according to the present invention are ionic liquids that are not miscible with water. That means the ionic liquids suitable for the method according to the present invention form a two-phase system when mixed with water at temperatures between 20 and 80° C. Hydrophobic ionic liquids that are not miscible with water are for example disclosed in U.S. Pat. No. 5,827,602.

The ionic liquids used according to the invention are preferably liquids, i.e. preferably they are liquids at room temperature (about 25° C.).

In a preferred embodiment, the anion $A^-$ of the water-immiscible ionic liquid is selected from the group comprising imides of the general formula $[N(R_f)_2]^-$ or of the general formula $[N(XR_f)_2]^-$ and $PF_3(R_f)_3$ where $R_f$ denotes partially or fully fluorine-substituted alkyl having 1 to 8 C atoms and X denotes $SO_2$ or CO. In a very preferred embodiment, the anion $A^-$ of the water-immiscible ionic liquid is tris(pentafluorethyl)trifluorophosphate [Fap] or especially preferred it is bis(trifluormethylsulfonyl)imide [Ntf$_2$].

It has been found that the anion $A^-$ of the water-immiscible ionic liquid is of more importance for determining whether an ionic liquid is especially suitable for the method of the present invention than the cation. It has been found that ionic liquids having a tris(pentafluorethyl)trifluorophosphate [Fap] and especially those having a bis(trifluormethylsulfonyl)imide [Ntf$_2$] anion, not only provide for a water-immiscible phase when combined with suitable cations but also provide for an enrichment of the nucleic acids in the aqueous phase.

When using a [Fap] or [Ntf$_2$] anion, the cation of the water-immiscible ionic liquid is preferably selected from the group comprising

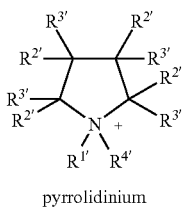

pyrrolidinium where the substituents $R^{1'}$ to $R^{4'}$ each, independently of one another, denote hydrogen or straight-chain or branched alkyl having 1-20 C atoms,
and
phosphonium cations according to formula (2)

$$[PR^2_4]^+ \qquad (2),$$

where $R^2$ in each case, independently of one another, denotes
H, or straight-chain or branched alkyl having 1-20 C atoms.

Preferred water-immiscible ionic liquids to be used in the present invention are Trihexyl(tetradecyl)phosphoniumtris(pentafluorethyl)trifluorophosphate [Ttp][Fap], Trihexyl(tetradecyl)phosphonium bis(trifluormethylsulfonyl)imide, N-Butyldiethanolammonium bis(trifluormethylsulfonyl)imide and especially preferred 1-Butyl-1-methylpyrrolidiniumbis(trifluormethylsulfonyl)imide [bmpyrr][Ntf$_2$].

The present invention relates to a method for lysing cells by thermal lysis in the presence of at least one water-immiscible liquid. The liquid is not only used during thermal lysis but also—and that is even more important—for the isolation of the nucleic acids from the mixture after lysis. Examples of suitable water-immiscible liquids are oils and ionic liquids.

The sample with the cells to be lysed is contacted with a lysis solution comprising at least one water-immiscible liquid. Typically, the sample is contacted with a volume of the lysis solution that at least equals the volume of the sample. That means, for example, if the sample has a volume of 5 μl, it is at least contacted with 5 μl of lysis solution. In a preferred embodiment, the volume of the lysis solution is at least 3-fold the volume of the sample. In a very preferred embodiment, it is at least 5-fold the volume of the sample.

In a preferred embodiment, the lysis solution only comprises one water-immiscible liquid but it can also comprise additional substances like one or more additional water-immiscible liquids. In a preferred embodiment, the lysis solution at least comprises one water-immiscible ionic liquid.

The mixture of the sample and the lysis solution is then heated to a temperature above 80° C. for thermal lysis. In a preferred embodiment, it is heated to a temperature between 80 and 200° C., very preferably it is heated to a temperature between 100 and 150° C.

Heating can be done by any means known to the person skilled in the art, e.g. in a heating block, with microwave radiation, a heating mantle or with ultrasound.

Typically the mixture is incubated for a short time at the temperature to which it was heated. The incubation time typically ranges from 2 seconds to 5 minutes depending on the temperature that was chosen, on the type of cell to be lysed and on the volume of the mixture.

For the extraction of the nucleic acids, the mixture is then contacted with water or an aqueous buffer solution. In case the mixture of the sample and the lysis solution had been heated to a temperature above 100° C., the mixture should be cooled to a temperature below 100° C. before adding the water or an aqueous buffer solution.

In a preferred embodiment, independent from the temperature at which the thermal lysis has taken place, the mixture is afterwards cooled down to a temperature below 50° C., preferably to a temperature between 4-40° C., most preferable between 20 and 40° C., prior to the addition of the water or an aqueous buffer solution.

The addition of water or an aqueous buffer solution to the mixture results in the formation of a two phase system—one phase comprises the water-immiscible liquid, one phase is an aqueous phase comprising the water or the aqueous buffer solution.

The pH of the water or the aqueous buffer solution that is added typically is between pH 4 and pH 12. In a preferred embodiment, it is between pH 6 and pH 10, most preferred between pH 6.5 and pH 8.5.

Typically, there is no limit to the amount of water or aqueous buffer solution that is added to the mixture of the sample and the lysis solution. Preferably, the volume of the water or aqueous buffer solution is between $\frac{1}{10}^{th}$ and 10-fold the volume of the mixture of the sample and the lysis solution. That means the volume ratio preferably is between 1:10 and 10:1. In a very preferred embodiment, it is between 1:2 and 2:1.

After adding the water or the aqueous buffer solution, the mixture is preferably agitated to provide a thorough mixing of the two phases. This can e.g. be done by shaking or vortexing.

Cellular debris as well as denaturated proteins are often found in the interphase between the aqueous and the water immiscible liquid phase. The aqueous phase can be separated and the nucleic acids can be isolated from the aqueous phase or the aqueous phase can directly be used for further evaluation, e.g. for real-time PCR.

It has been found that especially ionic liquids with an [Ntf$_2$] anion provide for an enrichment of the nucleic acids in the aqueous phase. When using other water-immiscible ionic liquids or oils according to the invention, the amount of nucleic acids that can be found in the aqueous phase is typically about 50% or more, but when using ionic liquids with an [Ntf$_2$] anion the amount of nucleic acids in the aqueous phase can typically be enlarged to more than 70% (of the total amount of nucleic acid in the mixture).

In a preferred embodiment, prior to adding the lysis solution, the sample can be preincubated with substances that support lysis. Substances that support lysis are for example detergents, chaotropic substances or water-miscible ionic liquids. It has been found that a preincubation with substances comprising an ammonium cation, especially water-miscible ionic liquids comprising an ammonium cation is favourable especially for samples comprising gram-positive bacterial cells. Examples of suitable substances comprising an ammonium cation are those comprising a cation [NR$_4$]$^+$ according to formula (1)
where
R in each case, independently of one another, denotes
H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more R may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R' may be =H, non-, partially or perfluorinated C$_1$- to C$_6$-alkyl, C$_3$- to C$_7$-cycloalkyl, unsubstituted or substituted phenyl and X may be =halogen.

Suitable substances comprising a cation [NR$_4$]$^+$ according to formula (1) which are no ionic liquids are for example aqueous ammonia, (NH$_4$)$_2$SO$_4$, NH$_4$Cl, NH$_4$COOH.

In a very preferred embodiment, preincubation is performed with at least one N,N-dimethyl-2-hydroxyethylammonium [DMAE] based ionic liquid. The cation of these ionic liquids is [DMAE]. The anion preferably is selected from the group of propionate, acetate, octanoate, 2-hydroxyacetate, trifluoroacetate and 2-hydroxybutyrate. The most preferred ionic liquids for preincubation are N,N-dimethyl-2-hydroxyethylammonium-2-hydroxybutyrate and especially N,N-dimethyl-2-hydroxyethylammonium-propionate.

Preincubation is typically performed by adding the substances that support lysis, e.g. the ionic liquid, to the sample. The substances that support lysis can be added as pure substances or mixed with water or an aqueous buffer solution. The volume that is added is typically between 10-fold and 1/10$^{th}$ of the sample volume. If ionic liquids are used as lysis supporting substances they are preferably mixed with water or an aqueous buffer in advance and then added to the sample. The amount of ionic liquid in the aqueous phase is typically between 0.05 and 6 M, preferably between 0.5 and 2 M.

One can add one or more substances that support lysis to the sample.

After adding the substance or the substances that support lysis (e.g. the N,N-dimethyl-2-hydroxyethylammonium-propionate), the mixture is typically incubated for 5 to 30 minutes at temperatures between 20 and 100° C. In a preferred embodiment, incubation is performed for 10 to 20 minutes at a temperature between 70 and 90° C.

Afterwards, for performing the thermal lysis according to the present invention, the water-immiscible liquid is mixed with the sample and the substance that supports lysis.

In another preferred embodiment, after having performed the thermal lysis and after having added water or an aqueous buffer solution, the two phase system might be treated with a proteinase to set free nucleic acids which stick to proteins or cellular debris. The preferred proteinase for this is proteinase K. Typically the two phase mixture is incubated with the proteinase at temperatures between 20 and 60° C., preferably at around 56° C., for 10 to 60 minutes, preferably for 10 to 30 minutes. Afterwards, solid material might be removed by centrifugation. The aqueous phase with the nucleic acids can then be isolated and further analyzed. To inactivate the proteinase after use, the sample is typically treated with an inactivator or heated. Methods to inactivate proteinases are known to the person skilled in the art. A preferred method is heat inactivation by heating the sample to about 100° C. The proteinase treatment is especially useful to improve the yield when isolating genomic DNA. It is typically not necessary for the isolation of plasmids or shorter oligonucleotides which typically do not stick to proteins or cellular debris.

Typically the procedure according to the present invention provides for an aqueous phase in which the nucleic acid is present in a purity that is sufficient to directly do PCR, like real time PCR, electroporesis (agarose or polyacrylamide) or typical cloning techniques like ligation or restriction enzyme digest.

For certain applications which necessitate especially high purity or if the original sample comprises specific impurities, a third phase can be added to the mixture after lysis and phase separation. The third phase can for example be an organic solvent or a polymer phase which is not miscible with both, the water-phase and the water-immiscible liquid phase. If oil is used as water-immiscible liquid, the third phase can also comprise a water-immiscible ionic liquid, if the water-immiscible liquid comprises a water-immiscible ionic liquid, the third phase can e.g. be an oil. The third phase offers additional possibilities to extract impurities from the aqueous phase which could otherwise not be separated from the nucleic acids. Organic impurities can e.g. be extracted by adding a third phase made of organic solvent. Proteins can for example be removed by adding a phase comprising polymers.

Another possibility to further improve the purity of the nucleic acids is to adjust the pH, build up a density gradient or a salt gradient before separating the aqueous and the water-immiscible liquid phase so that side products are precipitated or moved to the interphase between the aqueous phase and the water-immiscible liquid phase. Especially if ionic liquids are used as water-immiscible liquid, centrifugation can also help to remove precipitated side products from the aqueous phase as the aqueous phase is on top of the ionic liquid phase.

The nucleic acids isolated with the method according to the present invention may be used for quantitatively or qualitatively determining the cells in the sample. This can be achieved, for instance by PCR methods, in particular by real time PCR, electroporesis (agarose or polyacrylamide) or typical cloning techniques like ligation or restriction enzyme digest.

In order to determine or to monitor the efficiency of the isolation procedure the sample can be spiked with a defined amount of nucleic acids.

The method according to the present invention significantly facilitates and speeds up cell lysis and nucleic acid extraction. The whole procedure typically takes between 10 and 20 minutes without preincubation or 50 to 60 minutes with preincubation. In addition, the two- or even three phase system provides for automatic removal of impurities, which either move to the water-immiscible liquid phase (like salts in case of using water-immiscible ionic liquids), are stuck in the interphase between the water-immiscible liquid phase and the aqueous phase (like larger proteins and the cellular debris) or can be removed by targeted addition of a third phase (e.g. organic impurities by the addition of an organic solvent) or other means.

The present invention is further directed to a kit for performing cell lysis comprising at least one container with a water-immiscible liquid and one container with a proteinase. In a preferred embodiment, the proteinase is proteinase K. In another preferred embodiment, the water-immiscible liquid is a water-immiscible ionic liquid. The kit may additionally comprise one container with at least one N,N-dimethyl-2-hydroxyethylammonium [DMAE] based ionic liquid, preferably with N,N-dimethyl-2-hydroxyethylammonium-propionate. A container is any box, bottle or other packaging means suitable to store and package the water-immiscible liquid, the oil or a proteinase. Suitable containers are known to a person skilled in the art.

The method according to the present invention offers a very fast and effective lysis system. The present invention is further illustrated by the following figures and examples, however, without being restricted thereto.

Figure 1:
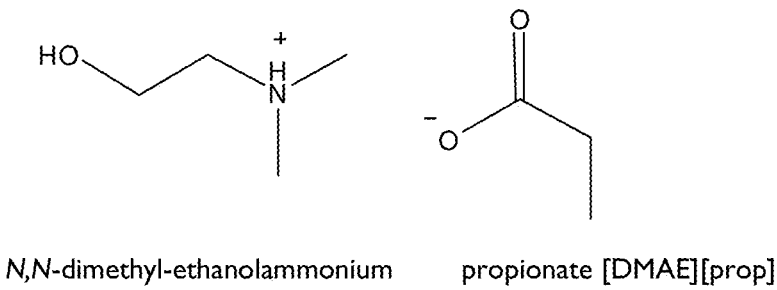
FIG. 1 show the chemical structure of ions being part of the preferred ionic liquids.
Figure 1:
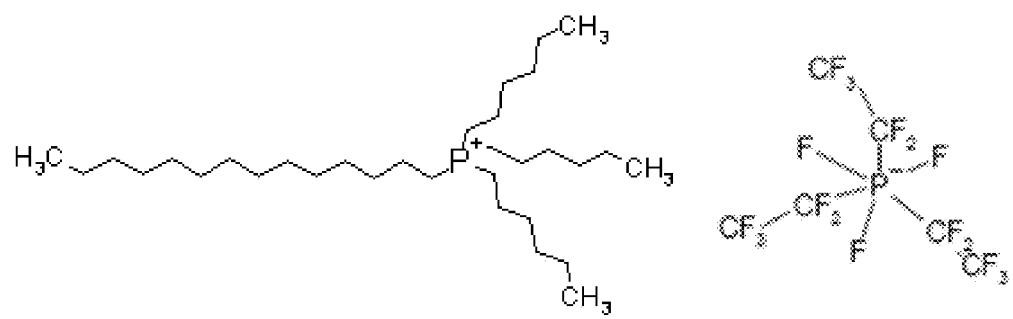
Figure 1:
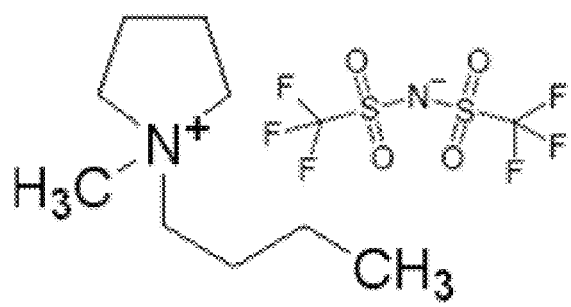
Figure 2:
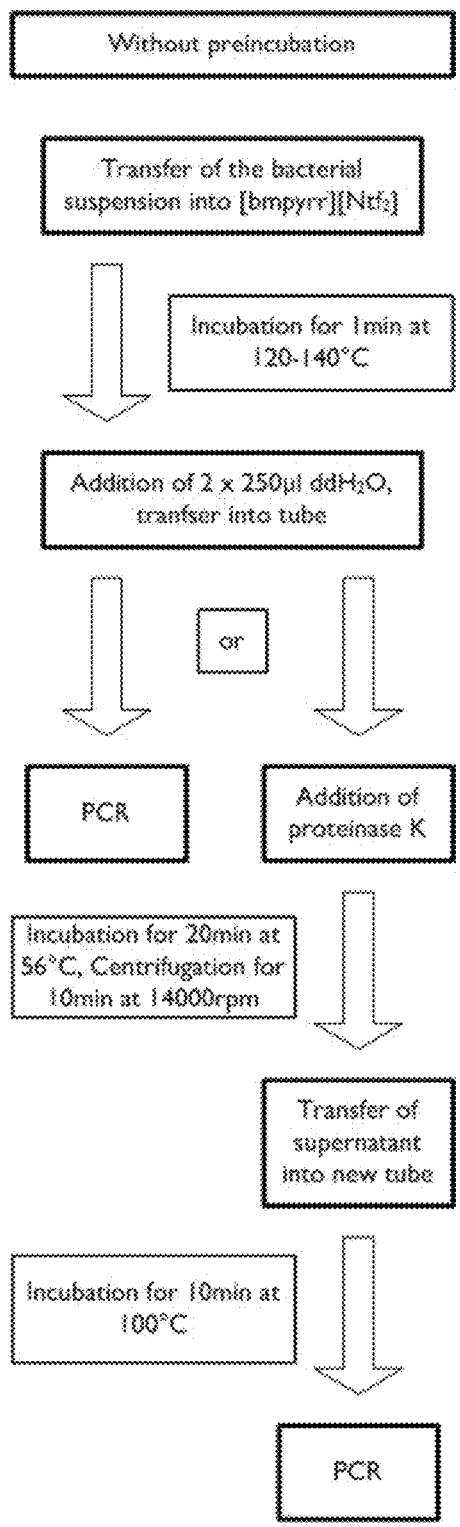
FIG. 2 gives one exemplary flow scheme for the procedural steps that are preferably performed when lysing gram-negativ cells with a lysis solution comprising a water-immiscible ionic liquid. In this case, typically, no preincubation is necessary.
Figure 3:
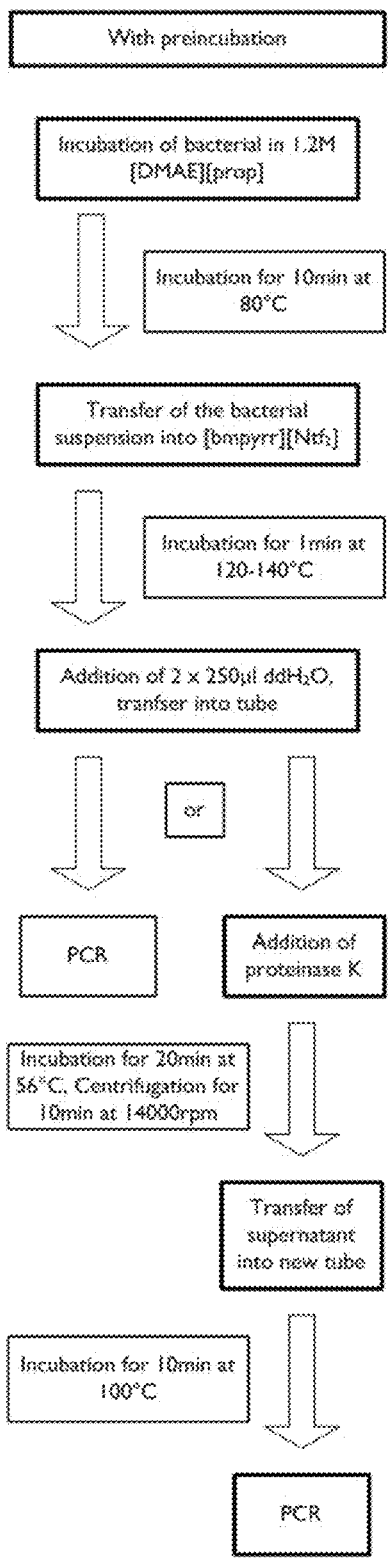
FIG. 3 gives one exemplary flow scheme for the procedural steps that are preferably performed when lysing gram-positive cells with a lysis solution comprising a water-immiscible ionic liquid. In this case, typically, a preincubation enlarges the yield of nucleic acids.

The entire disclosures of all applications, patents, and publications cited above and below and of corresponding EP application EP 11003449.3, filed Apr. 27, 2011, are hereby incorporated by reference.

Examples

The following examples represent practical applications of the invention.

Salmonella and Escherichia:
lysis: 1 min at 120 or 140° C. in 1-butyl-1-methylpyrrolidinium bis(trifluormethylsulfonyl)imide (bmpyrr $Ntf_2$)

Listeria:
preinkubation with N,N-dimethylethanolammonium propionate (DMAE prop) for 10 min at 80° C.
lysis: 1 min at 140° C. in 1-butyl-1-methylpyrrolidinium bis(trifluormethylsulfonyl)imide (bmpyrr $Ntf_2$)
afterwards: 20 min with Proteinase K Materials and Methods:
If not indicated otherwise, all chemicals and ionic liquids (ILs) were provided by Merck KGaA (Darmstadt, Germany).

Bacterial Strains and Culture Conditions.
L. monocytogenes EGDe (1/2a, internal number 2964) is used as model organism for Gram-positive bacteria. S. Typhimurium (NCTC 12023), E. coli TOP10F' and E. coli TOP10F', +ppl2/IAC (Frühwirth et al., 2011) are used as model organisms for Gram-negative bacteria. All strains are maintained at −80° C. using MicroBank technology (Pro-Lab Diagnostics, Richmond Hill, Canada). L. monocytogenes EGDe, S. Typhimurium and E. coli TOP10F', +ppl2/IAC are part of the collection of bacterial strains at the Institute of Milk Hygiene, Department of Veterinary Public Health and Food Science, University of Veterinary Medicine, Vienna, Austria. E. coli TOP 10 F' is provided by Invitrogen GmbH (Lofer, Austria). All bacterial strains are grown overnight in tryptone soy broth with 0.6% (w/v) yeast extract (TSB-Y; Oxoid, Hampshire, United Kingdom) at their respective optimal growth temperature 37° C.

Apparatus for Cell Disruption Experiments.
As tube for small volumes (100 µl) of ILs, a 0.3 ml glass micro cartridge for screw thread bottles (40×6 mm; Fisherbrand, Fisher Scientific Austria GmbH, Vienna, Austria), normally equipment for HPLC measurements is used.

For heating them above 100° C., an aluminium block with drilled holes fitting to the dimensions of the micro cartridges was fabricated and placed on a magnetic stirrer (IKAMAG® RCT; IKA-Labortechnik, Staufen i. Br., Germany). The actual temperatures are always measured directly with a metal thermometer (ama-digit ad14th, Amarell, Kreuzwertheim, Germany) sticking in a reference tube containing the respective IL.

Preparation of Bacteria and Cell Disruption Experiments

Gram Negative
Preparation of S. Typhimurium and E. coli. Bacteria of overnight cultures are harvested by centrifugation for 5 min at 6,000×g, washed three times with $ddH_2O$ and resuspended in 1/20 of the initial volume in $ddH_2O$. Ten µl of the resuspended culture are placed into 100 µl of bmpyrr $Ntf_2$, covered with a tinfoil and different incubation times and temperatures are tested. After incubation the "suspension" is transferred into a 2 ml tube (Eppendorf, Hamburg, Germany) by addition of 2×250 µl $ddH_2O$ to the IL and mixing with the pipette for a few seconds. The suspension is vortexed shortly and the upper phase is used directly for real-time PCR measurements.

Gram Positive

Preparation of L. monocytogenes. Bacteria of overnight cultures are harvested by centrifugation for 5 min at 6,000× g, washed three times with ddH$_2$O and resuspended in 1/20 volume of the initial volume in a 20% solution of DMAE propionate (time and temperature see Table 1). 10 µl of the resuspended culture are placed into 100 µl of bmpyrr Ntf$_2$ and different incubation times and temperatures are tested. After incubation the "suspension" is transferred into a 2 ml tube (Eppendorf, Hamburg, Germany) by addition of 2×250 µl ddH$_2$O to the IL and mixing with the pipette for a few seconds. The suspension is vortexed shortly and the upper phase is used directly for real-time PCR.

Control Samples for Cell Disruption Methods.

Ten microliter of the same bacterial suspension used in the cell disruption methods is used for DNA isolation using the NucleoSpin® tissue kit and the support protocol for Gram-positive bacteria. The step with the pre-lysis buffer (including lysozyme) is performed for one hour and the Proteinase K step is performed over night. The final step of the protocol is modified. Instead of one wash with 100 µl prewarmed (70° C.) elution buffer BE, two washes of 50 µl with prewarmed ddH$_2$O are used for elution of the DNA from the column (Mayrl et al., 2009). Finally 400 µl of ddH$_2$O are added to achieve the same volume as in the Cell disruption experiments.

DNA Standard for Real-Time PCR Quantification.

One milliliter of a pure overnight culture of each bacterial species is used for DNA isolation using the NucleoSpin® tissue kit and the support protocol for Gram-positive bacteria. The step with the pre-lysis buffer (including lysozyme) is performed for one hour and the Proteinase K step is performed over night. A modified protocol was used for the final step. Instead of one wash with 100 µl pre warmed (70° C.) elution buffer BE, two washes of 50 µl with pre warmed ddH$_2$O are used for elution of the DNA from the column (Mayrl et al., 2009). Determination of DNA concentration is performed by fluorimetric measurement using a Hoefer DyNA Quant 200 apparatus (Pharmacia Biotech, San Francisco, Calif., USA).

Real-Time PCR.

S. Typhimurium are analyzed according to previous publications (Mester et al., 2010; Roeder et al., 2010). Real-time PCR protocol for L. monocytogenes is carried out as published previously by targeting a 274 bp fragment of the prfA gene of L. monocytogenes (D'Agostino et al., 2004; Rossmanith et al., 2006). The plasmid ppl2/IAC containing an internal amplification control is analysed by real-time PCR according to the protocol for L. monocytogenes using a pLuc-LM5 probe (Fruhwirth et al. 2011). E. coli are analysed by a protocol of Kaclikova et. al. (2005).

Figure 4:
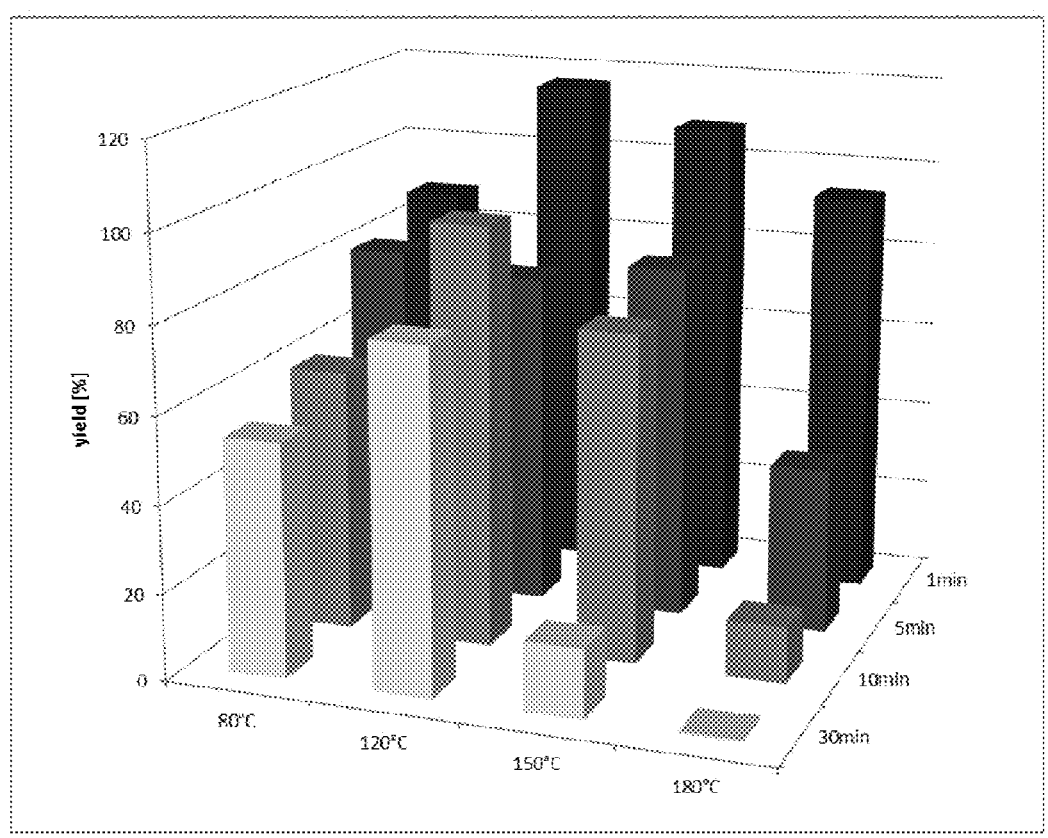
In FIG. 4, the results for different incubation temperatures and different incubation times are shown in comparison to a standard technique—Macherey&Nagel NucleoSpin® Kit—for lysis of Salmonella Typhimurium.

In FIG. 4, the results of the lysis protocol are presented for Salmonella Typhimurium for different incubation temperatures and incubation times Table 1 gives a summary of several reaction conditions for the extraction of genomic DNA from different bacterial strains.

Table 2 gives a summary of reaction conditions for the extraction of plasmid DNA from E. Coli.

In both tables the average yield (Av. Yield) is given in comparison to NucleoSpin® Tissue Kit.

TABLE 1

| Bacterial strains | Preincubation liquid | Incubation liquid | Incubation temperature/ time | Post-incubation | Av. Yield [%] |
|---|---|---|---|---|---|
| S. Typhimurium (NCTC 12023) | | bmpyrr Ntf$_2$ | 80° C./1 min | | 88 |
| | | bmpyrr Ntf$_2$** | 120° C./1 min | | 117 |
| | | bmpyrr Ntf$_2$ | 150° C./1 min | | 109 |
| | | bmpyrr Ntf$_2$ | 180° C./1 min | | 94 |
| | | rapeseed oil | 120° C./1 min | | 92 |
| E. coli TOP10F' | | bmpyrr Ntf$_2$ | 120° C./1 min | | 94 |
| | | bmpyrr Ntf$_2$ | 140° C./1 min | | 131 |
| | | bmpyrr Ntf$_2$ | 160° C./1 min | | 119 |
| | 1,2M DMAE prop, 10 min, 80° C. | bmpyrr Ntf$_2$ | 140° C./1 min | | 138 |
| L. monocytogenes (1/2a, internal n. 2964) | | bmpyrr Ntf$_2$ | 140° C./1 min | | 2 |
| | 1,2M DMAE prop, 10 min, 80° C. | bmpyrr Ntf$_2$ | 140° C./1 min | | 89 |
| | 1,2M DMAE prop, 10 min, 80° C. | bmpyrr Ntf$_2$ | 140° C./1 min | Proteinase K, 20 min, 56° C. | 98 |
| | 1,2M ammonia, 10 min, 80° C. | bmpyrr Ntf$_2$ | 140° C./1 min | Proteinase K, 20 min, 56° C. | 57 |
| | 1,2M DMAE 2-hydroxybutyrate, 10 min, 80° C. | bmpyrr Ntf$_2$ | 140° C./1 min | | 9 |
| | 1,2M DMAE 2-hydroxybutyrate, 10 min, 80° C. | bmpyrr Ntf$_2$ | 140° C./1 min | Proteinase K, 20 min, 56° C. | 64 |

TABLE 1-continued

| Bacterial strains | Preincubation liquid | Incubation liquid | Incubation temperature/ time | Post-incubation | Av. Yield [%] |
|---|---|---|---|---|---|
| | 1,2M DMAE trifluoroacetate, 10 min, 80° C. | bmpyrr Ntf$_2$ | 140° C./1 min | | 10 |
| | 1,2M DMAE trifluoroacetate, 10 min, 80° C. | bmpyrr Ntf$_2$ | 140° C./1 min | Proteinase K, 20 min, 56° C. | 30 |

TABLE 2

| Bacterial strain | Pre-incubation liquid | Incubation liquid | Incubation temperature/ time | Postincubation | Av. Yield [%] |
|---|---|---|---|---|---|
| E. coli Top10F', +ppl2/IAC | | bmpyrr Ntf$_2$ | 140° C./ 1 min | | 66 |
| | | bmpyrr Ntf$_2$ | 140° C./ 1 min | Proteinase K, 20 min, 56° C. | 44 |

RNA-Isolation
Reagents

For maintenance and growth of *Campylobacter jejuni* DSMZ 4866 brain heart infusion broth, glycerol, tryptic soy agar, yeast extract (Merck, Darmstadt, Germany), Columbia agar and laked horse blood (Oxoid, Basingstoke, UK) are purchased. DNA isolation is carried out with the Nucleo-Spin® tissue kit (Macherey-Nagel, Düren, Germany) and RNA isolation with the High Pure RNA isolation kit (Roche, Mannheim, Germany). The reagents used for real-time RT-PCR (SuperScript™ III reverse transcriptase, RNase™ OUT, SYTO9, PlatinumTaq® DNA polymerase) are obtained from Invitrogen (Lofer, Austria), and primers and probes from MWG Biotech (Ebersberg, Germany).

Culturing of *Campylobacter jejuni* (DSMZ 4688)

100 µl of a frozen permanent (20% v/v glycerol, 20% v/v laked horse blood and 60% v/v brain heart infusion broth, maintained at −80° C.) of the strain *C. jejuni* DSMZ 4688 are inoculated in 9 ml of brain heart infusion (membrane filtered) and grown under microaerobic conditions (3% O$_2$, 10% CO$_2$, 87% N$_2$) for 48 h at 42° C. For prove of purity of the culture, two plates of Columbia agar and trypton soy agar supplemented with yeast extract (0.6% w/v) respectively, are streaked out additionally and for prove of purity of the brain heart infusion broth 100 µl are plated on the same types of plate in each case.

RNA-Isolation from *C. jejuni* DSMZ 4688 by the Use of bmpyrr Ntf$_2$

In each case 1 ml of 48 h culture are harvested by centrifugation for 5 min at 6,000×g, and resuspended in 20 µl of DEPC treated H$_2$O and the whole amount placed into 100 µl of bmpyrr Ntf$_2$, covered with a tinfoil and incubated for one minute at 120° C. or 140° C. After incubation 100 µl DEPC treated H$_2$O or 90 µl DNase Incubation buffer and 10 µl DNase I (protocol according to High Pure RNA isolation kit) are added to the sample and the whole suspension is transferred into a 1.5 ml tube (Eppendorf, Hamburg, Germany). Additionally the suspensions are vortexed for a few seconds and the samples containing the DNase are first incubated for 60 min under shaking at room temperature and the DNase activity afterwards stopped at 75° C. for 15 min. In the meantime the samples treated with DEPC-treated H$_2$O, are cooled down with ice. The upper phase of the samples are transferred into a new tube after a final vortexing and stored at −80° C.

RNA-Isolation from *C. jejuni* by High Pure RNA Isolation Kit

For every sample 1 ml of 48 h culture are harvested by centrifugation for 5 min at 6,000×g, and treated according to the protocol of the High Pure RNA isolation kit. For estimation of the influence of the DNase I, this step is omitted in two samples.

DNA-Isolation and Reference for DNA Extraction from *C. jejuni* Via NucleoSpin® Tissue Kit One milliliter of 48 h culture is harvested by centrifugation for 5 min at 6,000×g, this sample is used as reference to obtain also the DNA content for comparison with the ionic liquid method. Additionally a sample is taken from a Columbia agar plate for producing a DNA standard. The DNA isolation is carried out according to the protocol of the NucleoSpin® tissue kit for gram positive bacteria (1 h lysozyme, proteinase K overnight). The final step of the protocol is modified. Instead of one wash with 100 µl prewarmed (70° C.) elution buffer BE, two washes of 50 µl with prewarmed ddH$_2$O are used for elution of the DNA from the column (Mayrl et al., 2009). The DNA concentration for the standard is obtained fluorimetrically by using a Hoefer DyNA Quant 200 apparatus (Pharmacia Biotech, San Francisco, Calif.).

Handling of Nucleic Acids for Quantification

The synthesis of the cDNA and the real-time RT-PCR analysis are performed according to the protocol of Dzieciol et al. (2011).

Table 3

The comparison of the performance of the present invention with a reference method (Commercial Kit RNA Isolation Kit) used for the isolation of RNA from *C. jejuni* is shown in Table 3. The reduced recovery of the protocol of the present invention with an additional DNAse step for digest and removal of the genomic DNA residues results from the duration of the DNAse protocol and not from an ostensive low RNA content. This is shown in table 5 presenting data proving a low DNA content. Therefore the RNA recovery of the present protocol as presented in this table is significant.

TABLE 3

| | copies per 5 µl | yield [%] |
|---|---|---|
| Standard method[a] | 8.54E+05 | |
| Standard method without Dnase-step | 9.74E+05 | |
| bmpyrr Ntf2 1 min 120° C. | 1.55E+06 | 181% |
| | 1.53E+06 | 179% |
| bmpyrr Ntf2 1 min 120° C. with DNase-step | 2.21E+05 | 26% |
| | 4.87E+04 | 6% |

TABLE 3-continued

|   | copies per 5 µl | yield [%] |
|---|---|---|
| bmpyrr Ntf2 1 min 140° C. | 1.62E+06 1.53E+06 | 190% 180% |
| bmpyrr Ntf2 1 min 140° C. with DNase-step | 2.24E+05 5.06E+05 | 26% 59% |

[a]High Pure RNA isolation kit (Roche, Mannheim, Germany)

Table 4

The recovery of genomic DNA during the experiments shown in Table 3 can be seen in Table 4.

TABLE 4

|   | copies per 5 µl | yield [%] |
|---|---|---|
| Standard method[a] | 6.10E+06 |   |
| bmpyrr Ntf2 1 min 120° C. | 2.74E+06 3.31E+06 | 45% 54% |
| bmpyrr Ntf2 1 min 140° C. | 3.11E+06 3.08E+06 | 51% 51% |

[a]NucleoSpin ® tissue kit (Macherey-Nagel, Düren. Germany), protocol for gram positive bacteria (1 h lysozyme, overnight proteinase K)

Table 5

The RT(−) value of the experiments shown in Table 3. The RT(−) value demonstrates the proportion of DNA in the sample after the protocol. For example a 2 log-scale interval means a DNA content of 1% in the sample.

TABLE 5

|   | log-scale interval |
|---|---|
| RNA isolation | 5.51 5.75 |
| RNA isolation without Dnase-step | 3.58 3.5 |
| bmpyrr Ntf2 1 min 120° C. | 2.67 2.75 |
| bmpyrr Ntf2 1 min 120° C. with DNase-step | 5.91 5.47 |
| bmpyrr Ntf2 1 min 140° C. | 2.67 2.78 |
| bmpyrr Ntf2 1 min 140° C. with DNase-step | 5.24 6.22 |

REFERENCE LIST

D'Agostino, M., Wagner, M., Vazquez-Boland, J. A., Kuchta, T., Karpiskova, R., Hoorfar, J., Novella, S., Scortti, M., Ellison, J., Murray, A., Fernandes, I., Kuhn, M., Pazlarova, J., Heuvelink, A., Cook, N., 2004. A validated PCR-based method to detect Listeria monocytogenes using raw milk as a food model—towards an international standard. J. Food Prot. 67, 1646-1655.

Dzieciol M., Wagner M., Hein I. (2011) CmeR-dependent gene Cj0561c is induced more effectively by bile salts that the CmeABC efflux pump in both human and poultry Campylobacter jejuni strains. Res Microb 162, p. 991-998.

Frühwirth K., Fuchs S., Mester P., Wagner M., Rossmanith P., 2011. Cloning and characterization of a -prfa Listeria monocytogenes strain containing an artificial single copy genomic internal amplification control (IAC). Food An. Meth. DOI: 10.1007/s12161-011-9212-6.

Kaclikova, E., Pangallo, D., Oravcova, K., Drahovska, H., Kuchta, T., 2005. Quantification of Escherichia coli by kinetic 5'-nuclease polymerase chain reaction (real-time PCR) oriented to sfmD gene. Lett. Appl. Microbiol. 41, 132-135.

Mayrl, E., Roeder, B., Mester, P., Wagner, M., Rossmanith, P. 2009. Broad range evaluation of the matrix solubilization (matrix lysis) strategy for direct enumeration of food-borne pathogens by nucleic acids technologies. J. Food Prot. 72, 1225-1233.

Mester, P., Wagner, M., Rossmanith, P., 2010. Use of Ionic Liquid-Based Extraction for Recovery of Salmonella Typhimurium and Listeria monocytogenes from Food Matrices. J. Food Prot. 73, 680-687.

Roeder, B., Wagner, M., Rossmanith, P., 2010. Autonomous growth of isolated single Listeria monocytogenes and Salmonella enterica serovar typhimurium cells in the absence of growth factors and intercellular contact. Appl. Environ. Microbiol. 76, 2600-2606.

Rossmanith, P., M. Krassnig, M. Wagner, I. Hein. 2006. Detection of L. monocytogenes in food using a combined enrichment/real-time PCR method targeting the prfA gene. Res. Microbiol. 157, 763-771.

The invention claimed is:

1. A method for lysing cells comprising
   a) providing a sample comprising the cells
   b) adding a lysis solution at least comprising a water-immiscible oil or a water-immiscible ionic liquid to the sample
   c) heating the mixture obtained in step b) to a temperature above 80° C.
   d) in case the temperature in step c) was above 100° C., cooling the sample to a temperature below 100° C.
   e) adding water or an aqueous buffer solution to the mixture, thereby obtaining a water-immiscible liquid phase and an aqueous phase.

2. A method according to claim 1, wherein the cells are bacterial cells.

3. A method according to claim 1, wherein in step c), the mixture is heated to a temperature between 100 and 150° C.

4. A method according to claim 1, wherein in step d), the sample is cooled to a temperature between 20 and 40° C.

5. A method according to claim 1, wherein the lysis solution added in step b) comprises a water-immiscible ionic liquid.

6. A method according to claim 5, wherein the anion of the ionic liquid is bis(trifluormethylsulfonyl)imide [Ntf$_2$].

7. A method according to claim 1, wherein the lysis solution added in step b) comprises Trihexl(tetradecyl)phosphoniumtris(pentafluorethyl)trifuorophosphate [Ttp][Fap] and/or 1-Butyl-1-methylpyrrolidiniumbis(trifluormethylsulfonyl)imide [bmpyrr][Ntf$_2$].

8. A method according to claim 1, wherein prior to adding the lysis solution, in a step b1) the sample is preincubated with at least one substance comprising an ammonium cation

[NR$_4$]$^+$ where
R in each case, independently of one another, denotes
H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more R may be partially or fully substituted by halogens, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R which are not in the α-position may be replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'— where R' is H, non-, partially or perfluorinated C$_1$- to C$_6$-alkyl, C$_3$- to C$_7$-cycloalkyl, or unsubstituted or substituted phenyl and X is halogen.

9. A method according to claim 1, wherein prior to adding the lysis solution, in a step b1) the sample is preincubated with at least one N,N-dimethyl-2-hydroxyethylammonium [DMAE] based ionic liquid.

10. A method according to claim 1, wherein after step e) the resulting mixture is incubated with a proteinase.

11. A method according to claim 1, wherein after step e) and an optional incubation with a proteinase the aqueous phase is directly analyzed by real-time PCR.

12. A method according to claim 1, wherein prior to adding the lysis solution, in a step b1) the sample is preincubated with at least one substance comprising an ammonium cation

[NR$_4$]$^+$ where
R in each case, independently of one another, denotes H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more R may be partially or fully substituted by —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R which are not in the α-position may be replaced by atoms and/or atom groups selected from the group consisting of —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'— where R' is H, non-, partially or perfluorinated C$_1$- to C$_6$-alkyl, C$_3$- to C$_7$-cycloalkyl, or unsubstituted or substituted phenyl and X is halogen.

13. A method for lysing cells comprising
a) providing a sample comprising the cells
b) adding a lysis solution at least comprising a water-immiscible liquid to the sample
c) heating the mixture obtained in step b) to a temperature above 80° C.
d) in case the temperature in step c) was above 100° C., cooling the sample to a temperature below 100° C.
e) adding water or an aqueous buffer solution to the mixture, thereby obtaining a water-immiscible liquid phase and an aqueous phase;
and wherein one or both of the conditions (i) or (ii) apply
(i) the lysis solution added in step b) comprises a water-immiscible ionic liquid, wherein the anion of the ionic liquid is bis(trifluormethylsulfonyl)imide [Ntf$_2$], or
(ii) the lysis solution added in step b) comprises Trihexl(tetradecyl)phosphoniumtris(pentafluorethyl)trifuorophosphate [Ttp][Fap] and/or 1-Butyl-1-methylpyrrolidiniumbis(trifluormethylsulfonyl)imide [bmpyrr][Ntf$_2$].

* * * * *